(12) United States Patent
Breitscheidel et al.

(10) Patent No.: US 6,207,865 B1
(45) Date of Patent: Mar. 27, 2001

(54) METHOD FOR THE HYDROGENATION OF CARBONYL COMPOUNDS

(75) Inventors: Boris Breitscheidel, Limburgerhof; Marc Walter, Frankenthal; Detlef Kratz, Heidelbeg; Gerhard Schulz, Ludwigshafen; Manfred Sauerwald, Meckenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/462,628

(22) PCT Filed: Jul. 15, 1998

(86) PCT No.: PCT/EP98/04402

§ 371 Date: Jan. 11, 2000

§ 102(e) Date: Jan. 11, 2000

(87) PCT Pub. No.: WO99/03801

PCT Pub. Date: Jan. 28, 1999

(30) Foreign Application Priority Data

Jul. 18, 1997 (DE) .............................................. 197 30 939

(51) Int. Cl.$^7$ ...................... C07C 29/136; C07C 29/141; C07C 29/145; C07C 29/149

(52) U.S. Cl. .......................... 568/705; 568/808; 568/809; 568/812; 568/814; 568/831; 568/832; 568/853; 568/857; 568/861; 568/863; 568/864; 568/881; 568/885

(58) Field of Search .................................... 568/705, 808, 568/809, 812, 814, 831, 832, 853, 857, 861, 863, 864, 881, 885

(56) References Cited

U.S. PATENT DOCUMENTS 4,300,003 * 11/1981 Mohring et al. ..................... 568/863
4,386,018 * 5/1983 Merger et al. ....................... 252/465
5,733,838 * 3/1998 Vicari et al. ......................... 502/335

* cited by examiner

Primary Examiner—Peter O'Sullivan
(74) Attorney, Agent, or Firm—Keil & Weinkauf

(57) ABSTRACT

A carbonyl compound or a mixture of two or more carbonyl compounds is catalytically hydrogenated in the presence of a Raney copper catalyst in the form of nuggets.

11 Claims, No Drawings

METHOD FOR THE HYDROGENATION OF CARBONYL COMPOUNDS

This application is a 371 of PCT/EP98/04402 filed Jul. 15, 1998.

The invention relates to a process for the catalytic hydrogenation of carbonyl compounds in the presence of a Raney copper catalyst.

Catalytic hydrogenation of carbonyl compounds, such as the hydrogenation of aldehydes to prepare simple and functionalized alcohols, occupies an important place in the production sequences in the basic chemicals industry. This is particularly true of the hydrogenation of aldehydes which can be obtained by the oxo synthesis or the aldol reaction.

Catalytic hydrogenation of aldehydes in a suspension or fixed bed procedure has been known for a long time. Industrial systems operate almost exclusively with fixed bed reactors.

The fixed bed catalysts used in particular are supported catalysts, for example Cu/Ni or Cu/Cr catalysts supported on $SiO_2$ or $Al_2O_3$.

Suitable alternatives to the supported catalysts are Raney-type catalysts. Raney catalysts show particularly high hydrogenation activity owing to the large surface area of metal. Suitable metals are nickel, cobalt, iron and copper.

SU 430 876 describes the hydrogenation of furfural on a Raney copper catalyst in a suspension procedure. Suspension processes have the disadvantage by comparison with fixed bed processes that the catalyst consumption is greater. It is furthermore necessary for the catalyst to be removed from the reaction mixture in an additional step.

RO 106 741 describes a process for the hydrogenation of furfural to furfuryl alcohol in a fixed bed reactor in a downflow procedure. Raney copper inter alia is employed as catalyst. The publication contains no information on the preparation of the catalyst and its properties.

JP-A-3 141 235 describes a process for the hydrogenation of acetone to isopropanole wherein a Raney nickel catalyst is employed. It is described that the Raney nickel catalyst is mixed with a Raney copper catalyst. At the same time, however, it is implicitly stated that when adding more than a certain amount of said catalyst, productivity will be decreased.

Raney catalysts which can be used in a fixed bed process are normally prepared by kneading an aluminum/copper alloy powder with binders and auxiliaries, producing moldings, for example tablets or extrudates, from the kneaded composition, calcining the moldings and activating the calcined moldings by treatment with an alkali metal hydroxide. Processes of this type for preparing Raney catalysts are described, for example, in DE-A 43 45 265, Ind. Eng. Chem. Res. 28 (1989) 1764–1767 and DE-A 44 46 907. Preparation of the catalyst by this process involves a plurality of steps.

It is an object of the present invention to provide a process for the catalytic hydrogenation of carbonyl compounds employing a catalyst which is easy to prepare industrially and has high activity and selectivity.

We have found that this object is achieved by employing Raney copper in the form of nuggets for the hydrogenation of carbonyl compounds to, for example, the corresponding alcohols with a high catalytic activity and selectivity exceeding the activity and selectivity of Raney copper catalysts prepared according to the prior art.

Accordingly the object has been achieved by a process for the catalytic hydrogenation of a carbonyl compound or of a mixture of two or more carbonyl compounds in the presence of a Raney copper catalyst, wherein the Raney copper catalyst is employed in the form of nuggets.

Nuggets mean that the metal is in the form of particles of irregular geometry with a size of from 0.5 to 10 mm. The Raney copper nuggets are produced from coarse-particle copper/aluminum alloy, without the intermediate steps of kneading the copper/aluminum alloy with a binder and/or auxiliary, shaping the kneaded composition to moldings and calcining the moldings, by treatment of the coarse-particle copper/aluminum alloy with alkali metal hydroxide.

The nuggets employed in the process according to the invention can be from 0.5 to 10 mm in size. They are preferably from 1 to 8 mm, particularly preferably from 2 to 7 mm, especially from 2 to 6 mm.

The Raney copper used in the process according to the invention is prepared starting from a copper/aluminum alloy. The copper/aluminum alloy is prepared in a manner known per se, for example by the process described in DE-A 21 59 736. The ratio by weight of aluminum to copper in the initial alloy is generally chosen in the range from 30:70 to 70:30% by weight, preferably from 40:60 to 60:40% by weight.

The Raney copper catalyst is prepared from the copper/aluminum alloy by dissolving out the catalytically inactive constituents with alkali metal hydroxide (activation). Preferred alkali metal hydroxides are sodium hydroxide or potassium hydroxide, and sodium hydroxide is particularly preferred. An aqueous solution of the alkali metal hydroxide is generally employed, preferably sodium or potassium hydroxide solution, particularly preferably sodium hydroxide solution, normally using a 5–30% by weight aqueous solution of the alkali metal hydroxide. The molar ratio of alkali metal hydroxide to aluminum is generally chosen in the range from 1:1 to 4:1, preferably from 1.5:1 to 2.5:1. The activation is normally carried out at from 25° C. to 95° C., preferably 45 to 90° C. The duration of the activation essentially depends on the required final aluminum content and is normally in the range from 10 to 30, preferably 15 to 25, h. The activation is expediently monitored by measuring the amount of hydrogen liberated during it. The activation process can also be carried out several times.

The starting material for the activation is normally the coarse-particle copper/aluminum alloy. The size of the copper/aluminum alloy particles can correspond to that of the Raney copper nuggets employed in the process according to the invention. However, it is also possible for the particles to be reduced to the required size after the activation.

The Raney copper catalysts employed in the process according to the invention preferably have a copper content of from 40 to 90% by weight, more preferably from 50 to 80% by weight, particularly preferably from 60 to 70% by weight.

The Langmuir specific surface area of the Raney copper catalysts employed in the process according to the invention is preferably from 5 to 50 $m^2/g$, more preferably from 15 to 40 $m^2/g$, particularly preferably from 20 to 40 $m^2/g$. The Langmuir surface area is determined by nitrogen absorption using the DIN 66 132 method.

A variable characteristic of the Raney copper catalysts according to the invention is also their specific Cu surface area (S—Cu). It is calculated from the $N_2O$ consumption measured on oxidation of surface copper atoms with gaseous $N_2O$ in a heated sample of the catalyst.

This is done by initially treating the sample with 10 mbar of $H_2$ at 240° C. for 4 hours. The pressure over the sample is then reduced to less than $10^{-3}$ mbar, and it is then treated with 30 mbar of $H_2$ for 3 hours, subsequently the pressure is again reduced to less than $10^{-3}$ mbar, followed by treatment with 100 mbar of $H_2$ for 3 hours, the pressure is again reduced to less than $10^{-3}$ mbar, followed by a final treatment with 200 mbar of $H_2$ for 3 hours, the hydrogen treatment in each case being carried out at 240° C.

In a second stage, the sample is exposed to $N_2O$ under a pressure of 266 mbar at 70° C. for 2 hours, the $N_2O$ being decomposed on the sample; the pressure over the sample is then reduced to less than $10^{-3}$ mbar, after which the increase in weight of the catalyst as a result of the formation of copper oxide on the surface thereof is determined.

The specific Cu surface area of the Raney copper catalysts is preferably from 0.5 to 7 m²/g, more preferably from 1 to 4 m²/g.

The pore volume of the Raney copper catalyst determined by mercury porosimetry is preferably from 0.01 to 0.12 ml/g, more preferably from 0.03 to 0.08 ml/g. The average pore diameter determined by this method is preferably from 50 to 300 nm, more preferably from 60 to 100 nm. The mercury pore volume and the pore diameter are determined by the DIN 66 133 method.

The apparent density of the Raney copper nuggets employed in the process according to the invention is generally from 1.9 to 2.4, preferably from 1.9 to 2.1, g/ml.

The process according to the invention can be carried out as fixed bed reaction with the catalyst in a fixed bed, or as fluidized bed reaction with the catalyst undergoing fluidization. The fixed bed is preferably used. The hydrogenation can be carried out in the gas phase or liquid phase. The hydrogenation is preferably carried out in the liquid phase, for example in a downflow or upflow procedure.

In a preferred embodiment of the process according to the invention with a downflow procedure, part of the product is, after passing through the reactor, continuously taken off as product stream, and the other part of the product is returned to the reactor together with fresh precursor containing the carbonyl compound. This procedure is referred to as the recycle procedure hereinafter.

In a downflow procedure, the liquid precursor containing the carbonyl compound to be hydrogenated is allowed to flow downwards over the catalyst bed which is arranged in the reactor, which is under a high pressure of hydrogen, with formation of a thin film of liquid on the catalyst. On the other hand, in an upflow procedure, hydrogen gas is passed into the reactor filled with the liquid reaction mixture, in which case the hydrogen passes through the catalyst bed as ascending gas bubbles.

In the upflow procedure, the process according to the invention can be carried out either batchwise or continuously. The process can be carried out continuously by taking off all the liquid product after passing through the reactor or else, in a similar manner to the procedure described above, taking off only part of the product and returning the other part of the product together with fresh precursor containing the carbonyl compound to the reactor (recycle procedure). The process is preferably carried out continuously, with all of the product being taken off after the precursor has passed once (straight) through the reactor.

The process according to the invention is suitable for the hydrogenation of carbonyl compounds such as aldehydes and ketones to give the corresponding alcohols, with aliphatic and cycloaliphatic saturated and unsaturated carbonyl compounds being preferred. In the case of aromatic carbonyl compounds there may be unwanted formation of byproducts due to hydrogenation of the aromatic nucleus. The carbonyl compounds may have other functional groups such as hydroxyl or amino groups. Unsaturated carbonyl compounds are generally hydrogenated to the corresponding saturated alcohols. The term "carbonyl compounds" used in connection with the invention includes all compounds which have a C=O group, including carboxylic acids and derivatives thereof.

The process according to the invention is preferably employed for the hydrogenation of aliphatic aldehydes, hydroxy aldehydes, ketones, acids, esters, anhydrides, lactones and sugars.

Preferred aliphatic aldehydes are branched and unbranched saturated and/or unsaturated aliphatic $C_2$–$C_{30}$ aldehydes as can be obtained, for example, by the oxo synthesis from linear or branched olefins with an internal or terminal double bond.

Examples of aliphatic aldehydes are:
propionaldehyde, n-butyraldehyde, isobutyraldehyde. valeraldehyde, 2-methylbutyraldehyde, 3-methylbutyraldehyde (isovaleraldhyde), 2,2-dimethylpropionaldehyde (pivalaldehyde), caproaldehyde, 2-methylvaleraldehyde, 3-methylvaleraldehyde, 4-methylvaleraldehyde, 2-ethylbutyaldehyde, 2,2-dimethylbutyraldehyde, 3,3-dimethylbutyraldehyde, caprylaldehyde and capraldehyde.

Besides the short-chain aldehydes mentioned, also particularly suitable are long-chain aliphatic aldehydes which can be obtained, for example, by oxo synthesis from linear α-olefins.

Enalization products are particularly preferred, eg. 2-ethylhexenal, 2-methylpentenal, 2,4-diethyloctenal or 2,4-dimethylheptenal.

Preferred hydroxy aldehydes are $C_3$–$C_2$ hydroxy aldehydes which can be obtained, for example, by aldol reaction from aliphatic and cycloaliphatic aldehydes and ketones with themselves or formaldehyde. Examples are 3-hydroxypropanal, dimethylolethanal, trimethylolethanal (pentaerythrital), 3-hydroxybutanal (acetaldol), 3-hydroxy-2-ethylhexanal (butyraldol), 3-hydroxy-2-methylpentanal (propionaldol), 2-methylolpropanal, 2,2-dimethylolpropanal, 3-hydroxy-2-methylbutanal, 3-hydroxypentanal, 2-methylolbutanal, 2,2-dimethylolbutanal and hydroxypivalaldehyde. Hydroxypivalaldehyde (HPA) and dimethylolbutanal (DMB) are particularly preferred.

Preferred ketones are acetone, butanone, 2-pentanone, 3-pentanone, 2-hexanone, 3-hexanone, cyclohexanone, isophorone, methyl isobutyl ketone, mesityl oxide, acetophenone, propiophenone, benzophenone, benzalacetone, dibenzalacetone, benzalacetophenone, 2,3-butanedione, 2,4-pentanedione, 2,5-hexanedione and methyl vinyl ketone.

It is also possible to react carboxylic acids and derivatives thereof, preferably those having 1–20 carbon atoms. The following may be mentioned in particular:

Carboxylic acids such as formic acid, acetic acid, propionic acid, butyric acid, isobutyric acid, n-valeric acid, trimethylacetic acid (pivalic acid), caproic acid, enanthic acid, caprylic acid, capric acid, lauric acid, myristic acid, palmitic acid, stearic acid, acrylic acid, methacrylic acid, oleic acid, elaidic acid, linoleic acid, linolenic acid, cyclohexanecarboxylic acid, benzoic acid, phenylacetic acid, o-toluic acid, m-toluic acid, p-toluic acid, o-chlorobenzoic acid, pchlorobenzoic acid, o-nitrobenzoic acid, p-nitrobenzoic acid, salicylic acid, p-hydroxybenzoic acid, anthranilic acid, p-aminobenzoic acid, oxalic acid, malonic acid, succinic acid, glutaric acid, adipic acid, pimelic acid, suberic acid, azelaic acid, sebacic acid, maleic acid, fumaric acid, 1,4-cyclohexanedicarboxylic acid, phthalic acid, isophthalic acid and terephthalic acid;

Carbonyl halides such as the chlorides or bromides of the abovementioned carboxylic acids, especially acetyl chloride or bromide, stearyl chloride or bromide and benzoyl chloride or bromide, which undergo dehalogenation in particular;

Carboxylic esters such as the $C_1$–$C_{10}$-alkyl esters of the abovementioned carboxylic acids, in particular methyl formate, ethyl acetate, butyl butyrate, dimethyl terephthalate, dimethyl adipate, methyl (meth)acrylate, butyrolactone, caprolactone and polycarboxylic esters such as polyacrylic acid polymethacrylic esters and their copolymers and polyesters, eg. poly(methyl methacrylate), carrying out in these cases in particular hydrogenolyses, ie. conversion of esters into the corresponding acids and alcohols;

Carboxylic anhydrides such as the anhydrides of the abovementioned carboxylic acids, in particular acetic anhydride, propionic anhydride, benzoic anhydride and maleic anhydride.

Carboxamides such as formamide, acetamide, propionamide, stearamide and terephthalarnide.

It is also possible to react hydroxy carboxylic acids such as lactic, malic, tartaric or citric acid, or amino acids such as glycine, alanine, proline and arginine.

The process according to the invention is particularly preferably employed for the hydrogenation of aldehydes and hydroxy aldehydes.

The carbonyl compound to be hydrogenated can be fed as gas or liquid into the hydrogenation reactor alone or as a mixture with the hydrogenation product, and the liquid can be in undiluted form or mixed with additional solvent. Particularly suitable additional solvents are water, alcohols such as methanol, ethanol and the alcohol produced under the reaction conditions. Preferred solvents are water, THF, NMP, and ethers such as dimethyl and diethyl ethers, MTBE, and water is particularly preferred.

The hydrogenation in both an upflow and a downflow procure is generally carried out at from 50 to 250° C., preferably at 70 to 200° C., particularly preferably at 100 to 140° C. under a pressure of from 15 to 250 bar, preferably 20 to 200 bar, particularly preferably 25 to 100 bar.

High conversions and selectivities are achieved with the process according to the invention. The catalyst employed has a higher activity than prior art catalysts. The hydrogenation can therefore be carried out with distinctly higher space velocities without loss of conversion and selectivity. In addition, the catalyst is simple to prepare because steps such as shaping and calcination are omitted. This makes the process according to the invention particularly economic.

The invention is explained in detail by the following examples

EXAMPLE 1
Hydrogenation of Hydroxypivalaldehyde (HPA) to Neopentyl Glycol (NPG) in a Downflow Procedure The initial solution comprises a mixture of 38% by weight HPA and 38% by weight NPG in 24% by weight water. This mixture was hydrogenated in a reactor with a length of 50 cm and an internal diameter of 4.25 cm (reactor volume 200 ml), charged with a) 200 ml of $Al_2O_3$-supported copper catalyst prepared as disclosed in EP-A 0 044 444 in tablet form (3×3 mm), Cu content 36% by weight, apparent density 1090 g/l, BET surface area 101 $m^2/g$, specific Cu surface area 11.5 $m^2/g$ as catalyst A, or b) 200 ml of $SiO_2$-supported copper catalyst prepared as disclosed in WO 95/32171 in bead form (diameter 3 mm), Cu content 18% by weight, apparent density 605 g/l, BET surface area 212 $m^2/g$, specific Cu surface area 9.8 $m^2/g$, as catalyst B, or c) 200 ml of Raney copper prepared as disclosed in DE-A 44 46 907 in tablet form (3×3 mm), Cu content 72% by weight, apparent density 2000 g/l, Langmuir surface area 24 $m^2/g$, specific Cu surface area 2.6 $m^2/g$, Hg pore volume 0.06 ml/g, average pore diameter (from Hg porosimetry) 84 nm, as catalyst C, or d) 200 ml of Raney copper in the form of nuggets (diameter 3 mm), Cu content 56% by weight, apparent density 1950 g/l, Langmuir surface area 26 $m^2/g$, specific Cu surface area 3.1 $m^2/g$, Hg pore volume 0.07 ml/g, average pore diameter (from Hg porosimetry) 92 nm, as catalyst D (according to the invention)

at a space velocity of 0.351 HPA/l catalyst×h at 130° C. under 35 bar in the downflow and recycle procedures (recycling 9.5 l/h).

EXAMPLE 2
Hydrogenation of 2,2-dimethylolbutanal (DMB) to 1,1,1-trimethylolpropane in an Upflow Procedure The initial solution was a 45% by weight aqueous DMB solution. This solution was hydrogenated in an upflow procedure in a reactor with a length of 30 cm and an internal diameter of 2.5 cm charged with 150 ml of catalyst B, C or D (according to the invention) from Example 1 at 120° C. under 90 bar. The solution was pumped straight through the reactor with various space velocities: 0.2, 0.3, 0.4 and 0.6 kg DMB/l catalyst×h.

Table 1 summarizes the results.

The results make it clear that the highest conversions and selectivities are achieved with catalyst D under conditions which are otherwise identical.

TABLE 1

| Catalyst | Precursor | Procedure | Space velocity kg/$l_{CAT}$·h | Conversion (from the GC % areas) % | Selectivity (from the GC % areas) % |
|---|---|---|---|---|---|
| A | HPA | downflow/recycle | 0.35 | 86.8 | 89.1 |
| B | HPA | downflow/recycle | 0.35 | 94 | 92.5 |
| B | DMB | upflow | 0.2 | 99.44 | 78.91 |
| B | DMB | upflow | 0.3 | 90.84 | 75.28 |
| C | HPA | downflow/recycle | 0.35* | 95.2 | 93.3 |
| C | DMB | upflow | 0.2 | 100 | 89.97 |
| C | DMB | upflow | 0.4 | 97.65 | 87.34 |
| C | DMB | upflow | 0.6 | 88.79 | 74.52 |
| D | HPA | downflow/recycle | 0.35 | 96.8 | 94.2 |
| D | DMB | upflow | 0.2 | 100 | 91.17 |
| D | DMB | upflow | 0.4 | 100 | 90.7 |
| D | DMB | upflow | 0.6 | 95.45 | 87.3 |

*$l_{HPA}$/$kg_{cat}$·h

We claim:

1. A process for the catalytic hydrogenation of a carbonyl compound or of a mixture of two or more carbonyl compounds in the presence of a Raney copper catalyst, wherein the Raney copper catalyst is employed in the form of nuggets and wherein the nuggets are particles of irregular geometry with a size of 0.5 to 10 mm.

2. A process as claimed in claim 1, wherein the Raney copper catalyst has the following properties:

size of the nuggets from 2 to 7 mm copper content from 40 to 90% by weight

Langmuir surface area from 5 to 50 m$^2$/g

Cu surface area from 0.5 to 7 m$^2$/g

Hg pore volume from 0.01 to 0.12 ml/g average pore diameter from 50 to 300 nm.

3. A process as claimed in claim 1, wherein the catalytic hydrogenation is carried out as fixed bed reaction in a downflow procedure.

4. A process as claimed in claim 1, wherein the catalytic hydrogenation is carried out as fixed bed reaction in an upflow procedure.

5. A process as claimed in claim 3, wherein the process is additionally carried out in a recycle procedure.

6. A process as claimed in claim 4, wherein the process is additionally carried out in a recycle procedure.

7. A process as claimed in claim 3, wherein the hydrogenation is carried out at from 70 to 200° C. under a pressure of from 20 to 200 bar.

8. A process as claimed in claim 4, wherein the hydrogenation is carried out at from 70 to 200° C. under a pressure of from 20 to 200 bar.

9. A process as claim in claim 1, wherein an aliphatic aldehyde or an aliphatic hydroxy aldehyde or a mixture of two or more thereof is employed as carbonyl compound.

10. A process as claimed in claim 9, wherein hydroxypivalaldehyde or dimethylolbutanal is employed as carbonyl compound.

11. A process as claimed in claim 1, wherein water is present as solvent.

\* \* \* \* \*